United States Patent
van Rijn et al.

(10) Patent No.: US 8,536,144 B2
(45) Date of Patent: *Sep. 17, 2013

(54) ANTI-FUNGAL COMPOSITION

(75) Inventors: Ferdinand Theodorus Jozef van Rijn, Delft (NL); Willem Johannes Wildeboer, The Hague (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/453,833

(22) Filed: Apr. 23, 2012

(65) Prior Publication Data

US 2012/0207860 A1 Aug. 16, 2012

Related U.S. Application Data

(63) Continuation of application No. 12/067,208, filed as application No. PCT/EP2006/066909 on Sep. 29, 2006, now Pat. No. 8,187,844.

(30) Foreign Application Priority Data

Oct. 4, 2005 (EP) ..................................... 05109190

(51) Int. Cl.
*A61K 31/70* (2006.01)
*C07H 17/08* (2006.01)

(52) U.S. Cl.
USPC ............................................. 514/31; 536/6.5

(58) Field of Classification Search
USPC ......................................................... 536/6.5
See application file for complete search history.

(56) References Cited

U.S. PATENT DOCUMENTS

| | | | |
|---|---|---|---|
| 4,073,923 A * | 2/1978 | Balasubramanyan et al. ............................. | 514/399 |
| 5,552,151 A | 9/1996 | Noordam et al. | |
| 5,597,598 A | 1/1997 | van Rijn et al. | |
| 5,738,888 A | 4/1998 | Cirigliano et al. | |
| 5,821,233 A | 10/1998 | Van Rijn et al. | |
| 5,962,510 A | 10/1999 | De Haan et al. | |
| 5,997,926 A | 12/1999 | van Rijn et al. | |
| 6,150,143 A | 11/2000 | Raghoenath et al. | |
| 6,228,406 B1 | 5/2001 | Borzuta | |
| 6,228,408 B1 | 5/2001 | Van Rijn et al. | |
| 6,369,036 B1 | 4/2002 | Van Rijn et al. | |
| 6,655,081 B1 | 12/2003 | Stark et al. | |
| 7,816,332 B2 | 10/2010 | Stark et al. | |
| 2005/0042341 A1 | 2/2005 | Thomas et al. | |
| 2005/0191397 A1 | 9/2005 | Williams et al. | |

FOREIGN PATENT DOCUMENTS

| | | |
|---|---|---|
| CA | 2243231 A1 | 1/1999 |
| EP | 1239732 A1 | 9/2002 |
| WO | 93/01720 A1 | 2/1993 |
| WO | 93/03170 A1 | 2/1993 |
| WO | 95/27073 A1 | 10/1995 |
| WO | 97/29207 A1 | 8/1997 |
| WO | 02/060501 A2 | 8/2002 |
| WO | 2005/018322 A1 | 3/2005 |

OTHER PUBLICATIONS

J. Stark, Natamycine en schimmelprolemem in de kaasindustrie, Microbiology, Apr. 1999, Abstract.
Stark (1995), Penicillium discolor. Symposiumbook "Voorkoming van ongewenste schimmelgroei op kaas": 15-18 (Article in Dutch).
Stark (1997), Moulds in cheese industry. Abstract book "World Congress on Food Hygiene". (lecture on symposium; Article in Dutch).
Frisvat et al. (1997), Penicillium discolor, a new species from cheese nuts and vegetables. Antonie van Leeuwenhoek 72:119-126.
Stark (1997), Schimmelbestriding in de Nederlandse kassindustrie. De Ware(n)-Chemicus 27: 173-176. (Article in Dutch).
Van Rijn et al. (1997), Penicillium discolor in de Nederlandse kassindustrie. Voedingsmiddlentechnologie 30:19-23. (Article in Dutch).
Hoeksta et al. (1998), Survey of the fungal flora in Dutch cheese factories and warehouses. Journal of Food Mycology 1:13-22.
Stark (1999), Natamycine en schimmelprolemen in de kassindustrie. Abstract book symposium "Resistentieproblematiek en ecologie van voedselgeralateerde micro-organismen". (Article in Dutch).
Stark (1999), Permitted preservatives—Natamycin. Encyclopedia of Food Microbiology (Academic Press, ed. Robinson et. al) vol. 3:1776-1781. (Review).
Dutreux et al. (2003) Growth prevention of mycotoxin-forming moulds on food products using Delcocid®. Poster presented at the seconds world mycotoxin forum in Noordwijk (Feb. 17-18, 2003).
Stark (2003), Natamycin, an effective fungicide for food and beverages. In: Natural antimicrobials for the minimal processing of foods. (Woodhead Publishing in Food Science and Technology, ed. S. Roller):82-97. (Review).
Stark and Tan (2003). Natamycin. In: Food Preservatives 2nd edition (Kluwer Academic, ed. G. Gould): 179-195. (Review).
Stark (2007). How can I protect my food with a preservative? In: Food Mycology 2007: emerging mold problems and spoilage in food and beverages (Ed. R. A. Samson et al.): 19.
Stark (2007). Cheese and fermented sausages. In: Food Mycology, a multifaceted approach to fungi and food (CRC Press, ed. J. Dijksterhuis and R. A. Samson). V25: 319-331. (Review).
Hary Brik, "Natamycin", Analytical Principles of Drug Substances, vol. 10, (1961) Academic Press, Inc., pp. 513-561.

* cited by examiner

*Primary Examiner* — Elli Peselev
(74) *Attorney, Agent, or Firm* — Baker Donelson Bearman Caldwell & Berkowitz PC

(57) ABSTRACT

The present invention relates to an improved anti-fungal composition, to a process for preparing it and to its use as a preservative.

9 Claims, No Drawings

ANTI-FUNGAL COMPOSITION

This application is a Continuation Application of U.S. application Ser. No. 12/067,208 filed Jun. 3, 2008, now U.S. Pat. No. 8,187,844, which is a National Stage Application of PCT/EP06/66909 filed Sep. 29, 2006 which claims priority to European Patent Application No. 05109190.8 filed Oct. 4, 2005, each hereby incorporated by reference in their entireties.

FIELD OF THE INVENTION

The present invention relates to an improved anti-fungal composition, to a process for preparing such an anti-fungal composition and to its use.

BACKGROUND OF THE INVENTION

The need for improved food preservation methods is great. It has been estimated that about one quarter of the world's food supply is lost as a result of microbial spoilage and food-borne microbial infections represent a constant and serious threat to human health.

Fungal spoilage can lead to serious economic losses. Several food products e.g. agricultural products, dairy and meat products, fruits and vegetables and derived products, bakery products and cosmetics are very susceptible to fungal growth. Examples of dairy products are cheese, cottage cheese, ricotta and yoghurt. Dried cured sausages are an example of meat products. Examples of agricultural products are crops such as cereals, nuts, fruits, vegetables and flower bulbs. Spoilage by fungi does not only affect the quality of the product, but also represents a health risk. It is well known that some fungal species, which grow on e.g. dairy products and sausages, can produce mycotoxins. Some mycotoxins are extremely dangerous as they can cause lethal diseases. Therefore the outgrowth of unwanted fungi in and on food products should always be prevented.

Food preservation techniques, e.g. heat processing, freezing, ultrasound, irradiation, and modified atmosphere packaging, significantly reduce microbial load but of particular concern is the evidence that processed foods are being contaminated with microorganisms following processing and prior to packaging. Of rising concern in the food industry is microbial spoilage of various foods such as dairy and meat products, dressings, spreads, margarines and seafood. Especially food products in the 2.0 to 7.0 pH range are known to be susceptible to microbial spoilage by yeast, fungi, acid tolerant bacteria and/or mesophilic or thermophilic spore forming and non-spore forming bacteria.

Mostly, processed foods are not eaten directly after processing thereby permitting bacteria, yeast or mould introduced by post-contamination to grow. Since food consumption may occur without reheating the processed foods to sufficient temperatures for sufficient time, there is a risk of food poisoning or food spoilage. Furthermore, the recent trend for minimally processed foods with the intrinsic nutritional and sensory qualities of raw and fresh foods has raised a new safety risk. Milder preservation treatments, such as high hydrostatic pressure and pulsed electric fields have proved to be successful but rely on effective hurdles i.e. cold chain and addition of natural anti-microbials.

There has been extensive research conducted in the field of food safety to develop effective anti-fungal compositions. Natamycin also known as pimaricin or tennecetin, is a polyene antibiotic, which has been known since the late fifties (Struyk et al, Antibiot. Ann. 1957-1958, 878) and which is currently used as a preservative in many food and agricultural products. U.S. Pat. No. 5,821,233 discloses natamycin exhibiting a high release rate of at least 3 µg/24 hours over the first 24 hours when contacted on a carrier with an agar surface of 0.6 cm diameter, and a carrier loading of 40 µg of natamycin. U.S. Pat. No. 5,997,926 discloses natamycin complexes with similar release rates. For some food applications, this kind of natamycin with a high release rate does not offer an adequate protection because for example the duration of the protection is not sufficient and/or the stability of the natamycin is not optimal. As a consequence, higher amount of natamycin would be needed to offer an adequate protection. Natamycin with a high release rate can also penetrate too far in the product treated, which could be unwanted in some products.

To control the release of natamycin, encapsulation has been proposed, see for example WO2005/018322 and US2005/042341. Encapsulation does not change the characteristics of the natamycin itself, but it tries to ensure a slower release of natamycin by applying an extra barrier. This automatically requires extra formulation steps after the recovery of the natamycin from a natamycin source, which makes the natamycin production process more complicated then when the natamycin itself would be changed to give a slower release.

Therefore, there is still a need for improved anti-fungal compositions that could solve at least some of these problems: slower release, longer duration of protection and/or improved stability.

DETAILED DESCRIPTION OF THE INVENTION

The present invention relates to an improved anti-fungal composition, especially a natamycin is provided, which exhibits a low natamycin release rate. This natamycin is preferably prepared using the process defined below.
Process for Preparing Natamycin Exhibiting a Low Natamycin Release Rate The present invention relates to a process for the production of the natamycin of the invention with a low natamycin release rate as defined below. In the process of the invention, natamycin is recovered from a fermentation broth containing biomass and natamycin and said process comprises:
(a) disintegrating the biomass;
(b) separating the natamycin from the thus treated fermentation broth to obtain a natamycin suspension;
(c) adjusting the pH of said natamycin suspension to a value greater than 10 and adding an amount of a substantially water-miscible solvent sufficient to dissolve the natamycin in said natamycin suspension;
(d) removing insoluble solids from said pH-adjusted natamycin solution;
(e) lowering the pH of said solution obtained in step (d) to a level sufficient to precipitate the natamycin and to form a natamycin suspension; and
(f) removing the natamycin from said natamycin suspension.
(g) Optionally, drying of the said removed natamycin
(h) And optionally reducing the size of the said dried natamycin.

The first advantage of the process according to the invention is that, without encapsulation or other way of complex processing, it leads to a natamycin product which has a slower release rate than high release natamycin formulations, such as U.S. Pat. Nos. 5,997,926 and 5,821,233, and other commercially available natamycin products, such as Delvocid® and Delvocid® Instant, as illustrated in the Examples. At the same time, the release rate is high enough to offer longer protection.

Surprisingly, the production process according to the invention leads to a product with new characteristics which could not have been anticipated from the prior art.

A second advantage is that the process maintains the advantage of earlier processes, see for example WO 97/29207, that natamycin is separated from the biomass and other impurities without using organic solvents, which is preferable from an environmental point of view.

Fermentations producing natamycin usually result in a fermentation broth comprising natamycin, biomass solids, dissolved or suspended nutrients, other fermentation products and water.

The fermentation broth in general contains of at least 2 g/l natamycin, preferably at least 7 g/l natamycin. For example the natamycin concentration in the fermentation broth can be about 7 g/l as disclosed in WO 93/03170. Since natamycin has a very low solubility in water under typical fermentation conditions, the natamycin in the fermentation broth is present in solid form. Preferably, the natamycin is mainly present in solid form. Mainly means at least 50%, preferably at least 70% and more preferably at least 80%. Solid natamycin means 'natamycin not dissolved in water'. The solid form of natamycin present in the fermentation broth may preferably comprise natamycin particles. Natamycin particles are natamycin crystals, which, for example, may have the following forms: needle-formed crystals, disc-formed crystals or the like. During the fermentation natamycin particles are formed. The natamycin particles usually have diameters ranging from 0.5-20 micrometer. The diameter of the natamycin particle is the largest distance from one part of the particle to the other end of the particle. Needle-formed natamycin particles with diameters of more than 40 micrometer have been observed. Diameters may be determined using a microscope. Preferably, in the process of the invention, the fermentation broth comprises natamycin particles having an average particle diameter of at least 2 micrometer, more preferably the natamycin particles have an average particle diameter of at least 5 micrometer and most preferably the natamycin particles have an average particle diameter of at least 10 micrometer.

The biomass of the *Streptomyces* organisms used in the production of natamycin generally consists of clusters (mycelia) of threads, although other forms of biomass, e.g. the so-called "pellets", may be present as well. In these threads (hyphae) compartments are present, in which cellular activities are localized. The size of these threads as present in the clusters is in general from 10-30 micrometer (diameters ranging from 0.5-1.0 micrometer).

According to a preferred process, the natamycin is mainly present in solid form in the fermentation broth. Preferably, at least 50% of the natamycin is present in solid form, more preferably at least 70%, even more preferably at least 80%.

Step (a)

In the present invention, the fermentation broth obtained at the end of the fermentation process is treated to disintegrate the biomass. Disintegration of the biomass may result in lysis, solubilisation of cell matters, and fragmentation (size reduction) of the clusters and threads. Disintegration of the biomass may be checked by viewing the biomass with a microscope (magnification 400×). Disintegration is complete if hardly any clusters or threads of the biomass can be observed through a microscope. Disintegration of the biomass can also be determined by measuring the viscosity of the fermentation broth. For example during the disintegration of a biomass of the cluster-type, the viscosity decreases. If the viscosity does not substantially decrease on further treatment, the biomass will be sufficiently disintegrated. Although different fermentation conditions or different *Streptomyces* organisms used in the production of natamycin may result in somewhat different forms of biomass present at the end of the fermentation, one skilled in the art is able to find a suitable duration for the disintegration of the biomass of any fermentation broth.

Homogenization, high shear mixing and ultrasonic techniques or heat-, pH-(alkaline), or enzymatic-treatments or treatment with surface-active agents can, for example, be used alone or in combination to disintegrate the biomass. The disintegration techniques are chosen in such a way that disintegration is obtained without substantially affecting the natamycin. Most of the natamycin, at least 80%, preferably up to 100%, keep their solid form and natamycin activity will not substantially reduce. Furthermore, it will be clear to one skilled in the art that the disintegration techniques may not substantially affect the natamycin particle size. If particle size of natamycin is reduced like the particle size of the biomass, then separation of the natamycin from the biomass would be difficult. An efficient example of disintegration is the use of a heat treatment optionally combined with a pH-treatment.

A heat treatment can be applied to the fermentation broth at the end of the fermentation (e.g. in the fermentor, after all supplies (e.g. oxygen, carbon or nitrogen sources) have ceased). The heat treatment may be carried out, for example, for 1 to 8 hours and, for example, at 30 to 50° C. Preferably the heat treatment may be carried out at 30 to 40° C. Higher temperatures may result in flocculation, precipitation and coagulation, which would adversely affect separation of the biomass from the natamycin particles.

A pH-treatment for, for example, 1 to 8 hours and, for example, at a pH of 8 to less than about 10 can also be easily conducted at the end of the fermentation in the fermentor. At pH's above 10 natamycin will become more soluble and more vulnerable to inactivation, which might adversely affect recovery yield and purity of the final natamycin. Sodium hydroxide or any other compatible caustic material, for example ammonium hydroxide or potassium hydroxide, can be used to increase the pH. After the alkaline incubation the broth is neutralized by hydrochloric acid or another compatible acid, for example phosphoric acid, sulphuric acid or acetic acid. Preferably, neutralization takes place after separating the natamycin from the fermentation broth.

Enzymatic-treatments can involve the incubation with cell wall decomposing and/or organic polymer decomposing enzymes such as lysozyme, xylanase, cellulase, protease, glucanase, lipase and amylase. The enzymes, alone or as mixtures of enzymes, are generally incubated under the optimum conditions for the enzymes to operate. The enzymes contribute to the lysis of cells and to the solubilization of organic polymers.

Homogenisation can involve the use of a Manton-Gaulin type homogenisator. The fermentation broth is forced through an orifice. Due to pressure forces the biomass will disintegrate.

Disintegration of the biomass by ultrasonic techniques can be obtained by applying ultrasonic waves to the fermentation broth, that will provide for oscillation of cell liquid which the cell walls cannot withstand. Disintegration of the biomass by high shear mixing involves the application of high shear forces to the biomass. These high shear forces can be obtained by stirring or other mechanical agitation. Certain fermentors may for example be equipped with stirring devices which are capable of providing the required high shear forces in order to disintegrate the biomass. During fermentation, stirring can be adapted to the optimal growth or natamycin production conditions for the biomass. After fermentation stirring can be adapted in order to disintegrate the biomass for example by applying high stirring velocities. High shear mixing may also for example be accomplished by using high shear Waring (or other) blenders.

Disintegration of the biomass by treatment with surface-active agents may involve for example the use of octylphenoxypolyethoxyethanol compounds, such as Triton type compounds. The fermentation broth may be incubated with for example 0.01 to 1% of for example Triton X-100 during for example 1 to 24 hours.

Step (b)

After the biomass disintegration-step, the natamycin is separated from the biomass to obtain a natamycin suspension. Due to the disintegration treatment, the biomass now mainly consists of small solid particles and/or solubilized matter. Where conventional separation techniques used in the recovery processes for fermentation products are mainly used to separate the solid from the liquid phase, the separation techniques preferably used in the present invention separate solid particles from the disintegrated biomass, for example on the basis of size differences and/or density differences. The separation techniques preferably used in the present invention will not result in a clear liquid phase, but will result in a troubled liquid phase that contains most of the smaller and/or less dense solid particles (mainly comprising the disintegrated biomass).

In order to separate the biomass from the natamycin particles the fermentation broth can, for example, be treated using a gravity gradient separation technique. The gravity gradient separation technique separates the natamycin particles from both soluble and insoluble impurities. Gravity gradient separation techniques include, for example gravity gradient centrifugation, and may, for example, use upflow columns and hydrocyclones. Gravity gradient separation techniques make use of the principle that particles of different densities and/or sizes can be separated when these particles of different densities and/or sizes are subjected to gravity or equivalent forces.

During the biomass disintegration the biomass particles become smaller. This makes it possible to separate the biomass from the natamycin particles. Usually more than 90% of the disintegrated biomass and other impurities can be removed with the gravity gradient separation technique. Separation efficiency can be increased by adding water and/or a salt (e.g. sodium chloride) to the disintegrated fermentation broth.

The use of gravity gradient separation techniques has the advantage that it is possible to easily modify or direct the process according to the desired purity and yield of the final product. By varying the operation conditions, the purity or the yield can be increased. In general when the purity increases, the yield will decrease and vice versa. The process according to the invention can for example provide natamycin of about 70 w/w % purity (anhydrous basis) on dry matter with a yield of about 90%. Using different process parameters natamycin of about 90 w/w % purity (anhydrous basis) on dry matter with a yield of about 80% can also be obtained with the process of the present invention. It is even possible to produce several products of different qualities from one fermentation broth.

Gravity gradient separation techniques will give better results, e.g. higher purities and/or yields, if the difference in particle density and/or size between the product particles and the impurities is increased. Therefore it is preferred that the fermentation broth contains natamycin particles having an average particle diameter of at least 2 micrometer. The diameter is preferably determined using a microscope. Preferably the average natamycin particle diameter is at least 5 micrometer, more preferably at least 10 micrometer. Fermentation broths containing natamycin particles with an average diameter of about 25 micrometer have been observed. Since natamycin may be present in the fermentation broth with diameters ranging from below 0.05 micrometer to about 40 micrometer, it will be clear to one skilled in the art that the smallest particles may be lost during separation. Furthermore, it will be clear to one skilled in the art that fractions of natamycin particles with large diameters of high purity may be obtained using the gravity gradient separation technique. The conditions under which the gravity gradient separation technique is operated determine which fraction of the natamycin will be recovered. In general larger natamycin particles can, for example, be obtained by using low shear conditions during the fermentation, or by seeding the fermentation with small natamycin particles or by prolonging the fermentation.

Gravity gradient centrifugation can be simulated on laboratory scale by operating a batchwise centrifuge for a shorter time or with a lower number of revolutions per minute as compared to the standard operation of the centrifuge, which would result in a clear separation of the solids from the liquids.

On a production scale the centrifuge is usually operated continuously. As compared to the standard operation of this type of centrifuge, the hold up time in the centrifuge is decreased in order to separate the natamycin from the disintegrated biomass. The lower the hold up time, the higher the purity and the lower the yield of the obtained natamycin. One skilled in the art is able to find a suitable hold up time corresponding to an optimized or desired purity:yield ratio.

At the end of step (b), the natamycin suspension obtained has preferably a total volume which is approximately 5 to 10% compared to the original fermentation broth and which contains preferably less than 20% v/v of rest of biomass. More preferably, the natamycin suspension obtained has a total volume which is approximately 6 to 8% compared to the original fermentation broth and which contains less than 15% v/v of rest of biomass. Most preferably, the natamycin suspension obtained has a total volume which is approximately 6 to 8% compared to the original fermentation broth and which contains less than 10% v/v of rest of biomass.

Step (c)

In a following step of the process of the invention, the pH of said natamycin suspension is adjusted to a value of at least 10 and an amount of a substantially water-miscible solvent sufficient to dissolve the natamycin in said natamycin suspension is added.

Preferably, the water-miscible solvent used in step (c) is selected from the group consisting of acetone, methanol, ethanol, propanol, isopropanol, propanediol, tetrahydrofuran.

According to a preferred embodiment, the pH of step (c) is adjusted to a value ranged between 10.0 and 11.0, preferably between 10.2 and 10.8, more preferably between 10.3 and 10.6 and most preferably adjusted to a value of about 10.4.

The pH of the natamycin suspension is preferably adjusted by adding an appropriate quantity of an alkaline agent such as NaOH, KOH, $Na_2CO_3$, $K_2CO_3$.

The addition of a water-miscible solvent and the increase of the pH of the natamycin suspension leads to a solution comprising dissolved natamycin.

Step (d)

Subsequently, any insoluble solids are removed from said pH-adjusted natamycin solution. The removal of the insoluble solids may be performed using any suitable method such as membrane filtration, depth filtration or centrifugation. One skilled in the art will be able to perform the insoluble solids removal using any of the techniques described above. Preferably, the removal of the remaining debris is made by membrane filtration followed by a depth filtration. After the membrane filtration, the filter cake is washed with a propanol solution to remove any dissolved natamycin from the cake. Preferably, the propanol solution is 35% v/v. Preferably, the depth filtration is realized on a filter having at least 0.4 µm pore diameter. More preferably, the filter has at least 0.25 µm pore diameter.

Step (e)

Subsequently, the pH of the natamycin solution is lowered to a level sufficient to precipitate natamycin and to form a natamycin suspension. Any acidic chemical can be used to lower the pH. An example of a suitable acidic chemical is hydrochloric acid. The pH is lowered to a value ranged between 5.0 and 8.0. Preferably the pH is lowered to a value ranged between 5.0 and 7.0, more preferably between 5.5 and 6.5. Most preferably, the pH is lowered to reach a value of about 6.0. Preferably, the pH is lowered using small pH steps in order to ensure the formation of crystalline crystals possessing high purity (preferably under continuous stirring).

A small pH step means preferably that the addition of a suitable quantity of an acidifying agent is added to reach a lowering of 0.1, preferably 0.2 and more preferably 0.3 unit of pH per 5 minutes. The pH is preferably lowered 0.3 unit of pH per 5 minutes until the solution becomes turbid. After stirring continuously at this pH, the pH is lowered with 0.3 pH units per 3 minutes until the pH is 6.0.

Optionally, before lowering the pH of the natamycin solution, the temperature of this solution may be increased from 20° C. to 35° C.

After crystallization the temperature of the natamycin slurry is lowered to 5° C. to increase the yield.

Step (f)

In a further step of the process of the invention, natamycin is removed from said natamycin suspension. Preferably, the natamycin is removed using a membrane filter press. After filtration, the natamycin is washed using a propanol solution and subsequently dried by aeration of the natamycin filter cake. Preferably, the propanol solution is 35% v/v. Preferably, the produced filter cake is once more suspended using a 70% propanol solution and subsequently filtered to further reduce the water content.

Step (g)

Optionally, after the separation step the natamycin suspension may, for example, be dried in order to obtain a dry product. Any convenient drying technique can be used, e.g. vacuum drying, conduction drying or convection drying. Since natamycin is stable in the crystalline form thereof [natamycin.3 $H_2O$], it is critical not to dry the product to a moisture content below about 7%. Vacuum drying is preferably conducted at about 40° C.

Preferably, the drying is performed using a Nauta-mixer operated under vacuum. Drying is finished when a temperature of 40° C. is reached. Preferably, after drying, the temperature of the natamycin is reduced to below 20° C. to prevent microbial growth of any possible contamination.

Step (h)

Optionally, the dried natamycin obtained in step (g) is crushed preferably using a hammer mill in order to obtain crystals having a diameter ranged between 1 to 50 µm, preferably 1 and 10 µm. According to a preferred embodiment, the natamycin is crushed as described in U.S. Pat. No. 6,576,617.

Natamycin

Surprisingly the natamycin obtainable by said process exhibits a low release rate and/or a decrease in release rate with respect to natamycin known in the art. Therefore, the invention also relates to a natamycin obtainable by said process described above. The natamycin according to the invention exhibits a low release rate and/or a decrease in release rate as defined below. According to a preferred embodiment, the natamycin of the invention is not incorporated in any specific formulation to get these features. It is the natamycin per se that exhibits these features. The skilled person will understand that the scope of the invention is not limited to natamycin prepared according to the process of the invention.

Natamycin Defined by Having a Specific Decrease in Release Rate

According to a preferred embodiment, the release rate of the natamaycin of the invention decreases by 1 to 45 percent after at least 9 days, when contacted on a carrier with an agar surface of 0.6 cm diameter, and a carrier loading of 5 to 40 µg of natamycin. More preferably, the release rate under these conditions decreases by 10 to 45 percent, even more preferably by 20 to 45 percent and most preferably by 40 to 45 percent.

Preferably, the release rate of the natamycin decreases by 1 to 45 percent after 9 days, when contacted on a carrier with an agar surface of 0.6 cm diameter, and a carrier loading of 40 µg of natamycin. More preferably, the release rate under these conditions decreases by 10 to 45 percent, even more preferably by 20 to 45 percent and most preferably by 40 to 45 percent after 9 days.

Even more preferably, the release rate of the natamycin decreases by 1 to 35 percent after 9 days, when contacted on a carrier with an agar surface of 0.6 cm diameter, and a carrier loading of 10 µg of natamycin. More preferably, the release rate decreases by 10 to 35 percent, more preferably by 20 to 35 percent and most preferably by 30 to 35 percent.

Natamycin Defined by Having a Specific Release Rate

According to another preferred embodiment, natamycin exhibits a release rate ranged between 6 and 10 percent of the initial carrier loading after at least 9 days, when tested on a carrier with an agar surface of 0.6 cm diameter, and a carrier loading of 5 to 40 µg of natamycin. More preferably, the release rate ranges between 6 and 8 percent, more preferably between 6 and 7 percent and most preferably between 6 and 6.5 percent.

Preferably, natamycin exhibits a release rate ranging between 0.60 and 0.90 µg/day after 11 days, when tested on a carrier with an agar surface of 0.6 cm diameter, and a carrier loading of 10 µg of natamycin. More preferably, the release rate ranges between 0.60 and 0.80, more preferably between 0.60 and 0.70 and most preferably between 0.60 and 0.65.

Even more preferably, natamycin exhibits a release rate ranging between 0.35 and 0.50 µg/day after 11 days, when tested on a carrier with an agar surface of 0.6 cm diameter, and a carrier loading of 5 µg of natamycin. More preferably, the release rate ranges between 0.35 and 0.45 and most preferably between 0.35 and 0.40.

According to a preferred embodiment, natamycin exhibits:
- a release rate which decreases by 1 to 45 percent after at least 9 days, when contacted on a carrier with an agar surface of 0.6 cm diameter, and a carrier loading of 5 to 40 µg of natamycin and/or,
- a release rate ranging between 6 and 10 percent of the initial carrier loading after at least 9 days, when tested on a carrier with an agar surface of 0.6 cm diameter, and a carrier loading of 5 to 40 µg of natamycin, and
- a release rate ranging between 0.1 and 2.0 µg per 24 hours over the first 24 hours, when contacted on a carrier with an agar surface of 0.6 cm diameter, and a carrier loading of 40 µg of natamycin. More preferably, the release rate is ranging between 0.5 and 2.0, more preferably between 1.0 and 2.0 and most preferably between 1.5 and 2.0 optionally, natamycin crystals have a diameter which ranges between 1 to 50 μm, preferably 1 and 10 μm.

According to a preferred embodiment, natamycin exhibits:

a release rate which decreases by 1 and 45 percent after at least 9 days, when contacted on a carrier with an agar surface of 0.6 cm diameter, and a carrier loading of 5 to 40 μg of natamycin and/or, a release rate ranging between 6 and 10 percent of the initial carrier loading after at least 9 days, when tested on a carrier with an agar surface of 0.6 cm diameter, and a carrier loading of 5 to 40 μg of natamycin, and a release rate ranging between 0.1 and 1.0 μg per 24 hours over the first 24 hours, when contacted on a carrier with an agar surface of 0.6 cm diameter, and a carrier loading of 10 μg of natamycin. More preferably, the release rate ranges between 0.2 and 1.0, more preferably between 0.4 and 1.0 and most preferably between 0.8 and 1.0.

optionally, natamycin crystals have a diameter which ranges between 1 to 50 μm, preferably 1 and 10 μm.

The test used to measure the natamycin release rate has been described in example 1 of this application. Briefly, the sample comprising natamycin is applied to a carrier. The carrier can be any material that provides unlimited water transport. Preferably, the carrier is a filter paper disc, more preferably the filter paper disc used in example 1. Subsequently, the carrier loaded with the natamycin composition is applied to the surface of an agar plate seeded with yeast or fungal cells (in example 1 *Saccharomyces cerevisiae* cells were used). The agar plate and the carrier are subsequently incubated at a temperature such that the natamycin is released into the agar. (in example 1, the temperature chosen is 6° C.) during 24 hours. After having removed the carrier from the agar plate, the agar plate is incubated under growth permitting conditions for said cells (in example 1, the temperature is 30° C.) during a chosen period. In this case, the period is 24 hours or 48 hours depending on the type of release rate desired to be determined. Finally, inhibition of cell growth in the agar due to the presence of the natamycin, which has been released from the carrier into the agar, is determined. The size of the inhibition zone is a measure of the natamycin released from the sample.

Natamycin with such a low natamycin release rate is very attractive for all applications wherein for example a long protection is desired. For example, in cheese or in sausages or in other meat products such as poultry or in seafood and bakery products wherein a protection of at least several weeks against moulds is desired.

According to a preferred embodiment, a water-miscible solvent is present with the natamycin of the invention. Preferably, the water-miscible solvent is selected from the group consisting of acetone, methanol, ethanol, propanol, propanediol, tetrahydrofuran and combinations thereof.

Use of the Natamycin of the Invention

The invention further relates to an anti-fungal composition comprising the natamycin of the invention exhibiting a low natamycin release rate. According to a preferred embodiment, the anti-fungal composition of the invention additionally comprises at least another anti-microbial agent selected from the group consisting of a weak acid preservative, sulphur dioxide, sulphite, nitrate, nitrite, dimethyl dicarbonate, biphenyl, diphenyl, orthophenylphenol, thiobendazole, an inorganic acid, an imidazole and a bacteriocin. All these components are already known to the person skilled in the art and briefly described below:

1. a weak acid preservative such as sorbic acid, propionic acid, benzoic acid, a p-hydroxybenzoic acids, lactic acid, citric acid, acetic acid or an alkali metal or alkali earth metal salt thereof;
2. a polyene anti-fungal compound, preferably natamycin;
3. sulphur dioxide or sulphites;
4. nitrate and nitrite;
5. dimethyl dicarbonate;
6. biphenyl, diphenyl, orthophenylphenol or thiobendazole;
7. an inorganic acid, such as hydrochloric acid;
8. an imidazole such as imazalil; and/or
9. any anti-fungal compound known in the art for use as a preservative for food products, crop protection or after-harvest treatment of fruits, vegetables orcereals, pharmaceutical or cosmetic products.
10. nisin or pediocin or lysozyme.

Preferably the anti-microbial agent is a weak organic acid preservative and/or natamycine. The weak organic acid preservative may be sorbic acid, propionic acid, benzoic acid, lactic acid, citric acid or an alkali metal or alkali earth metal salt thereof, or mixtures thereof. According to a more preferred embodiment, the anti-microbial agent is sorbic acid, potassium, or calcium sorbate; benzoic acid, sodium, potassium, or calcium benzoate; natamycine or mixtures thereof.

Anti-microbial composition comprising a bacteriocin will be active against bacteria. Nisin is a peptide-like antibacterial substance produced by microorganisms such as *Lactococcus lactis* subsp. *lactis*. It is mainly active against gram-positive bacteria. Nisin is non-toxic and is free of side effects. Nisin is a Generally Recognized as Safe (GRAS) substance and is widely used in a variety of foods. Examples of such products are processed cheese, milk, clotted cream, dairy desserts, ice cream mixes, liquid egg, hot-baked flour products, dressings and beer. Nisin is heat-stable and can stand sterilization temperatures with minimal loss of activity. The World Health Organization Committee on Biological Standardization has established an international reference preparation of nisin, the International Unit (IU hereinafter). Delvoplus® and Nisaplin®, brand names for nisin concentrates are distributed respectively by DSM and Danisco. Delvoplus® and Nisaplin® contain 2.5% of pure nisin or 1 million IU per gram. Effective levels of nisin to preserve food products range from 10 to 800 IU/g or 0.25 to 20 ppm of nisin.

The invention further relates to a product treated with the anti-fungal composition of the invention. The anti-fungal composition of the present invention can be used to treat a wide variety of food- and feed products such as cheese, shredded cheese, yoghurt, butter, processed meat products, sausages, cereals, vegetables, fruits, fruit products and ready to use meals. The anti-fungal composition may also be used for the treatment of beverages such as fruit juices, lemonades, ice-tea, wine and beer. Agricultural applications such as spraying in the field or in green houses or post-harvest treatment is also included in this invention. Examples of crops are cereals, fruits, vegetables, beans, nuts, herbs, flowers and plants. Also seeds, flower bulbs and seed potatoes can be treated with the anti-fungal composition of this invention. Examples of pharmaceutical or cosmetic applications are compositions for topical applications, lotions, creams, ointments, shampoos and soaps.

Preferably the natamycin of the invention is incorporated into a food coating. Preferably, the coating is used to coat a meat or dairy product. All coatings as described in EP 1 239 732B are herewith incorporated by reference in this context. Briefly, such a coating is preferably used in the coating of a cheese, a sausage or a derived product. All types of polymers described in this patent may also be used in a coating comprising the natamycin of the invention. Additionally, anti-oxidating agent and/or chelating agent as described in EP 1 239 732 B may also be added to the natamycin of the invention and/or to coating comprising the natamycin of the invention.

The invention also relates to the use of the anti-fungal composition of the invention for the treatment of a product susceptible to fungal spoilage. The invention additionally relates to a method for preserving a product susceptible to fungal spoilage by treating the product with the anti-fungal composition of the invention.

The present invention is further illustrated by the following examples, which should not be construed as limiting the scope of the invention.

EXAMPLES

Example 1

Microbiological Method for Determining the Availability of an Anti-Fungal Component This example describes a microbiological method for determining the availability of an anti-fungal component within an anti-fungal composition. In this example, natamycin is the anti-fungal component.

Filter paper discs (S&S Antibiotics Test Discs no. 321260) with a diameter of 0.6 cm were loaded with the preparation to be tested such that each disc was loaded with 40 µg of natamycin, e.g. 50 µl of a sample containing 800 ppm of the natamycin to be tested was applied to a disc. The discs were then put on agar, which was seeded with the *Saccharomyces cerevisiae* ATCC 9763. The petri dishes containing the agar were then stored for 24 hours at 6° C. to permit the natamycin to release into the agar. Under these conditions, *Saccharomyces* does not grow. As a reference, discs were freshly loaded with a range of known amounts of natamycin dissolved in aqueous methanol.

The next day, the sample discs were transferred to new petri dishes containing agar seeded with *Saccharomyces cerevisiae*. New discs freshly loaded with a range of known quantities of dissolved natamycin were prepared for use as a reference. The new dishes with the sample discs and the new reference were stored at 6° C. for 24 hours and the old dishes containing the released natamycin incubated at 30° C. for 24 hours.

The size of the inhibition zone is a measure of the natamycin released from the sample disc. The amount of released natamycin can be calculated by methods know per se. By repeating the procedure, the released natamycin can be measured on a daily basis. Other release time periods may alternatively be chosen.

Example 2

Production Process of Natamycin with Improved Properties

A fermentation broth of *Streptomyces natalensis* containing natamycin having an average particle diameter of about 10 micrometer was incubated at a temperature of 35° C. for 3 hours. This thermally treated broth was further treated to a gravity gradient centrifugation. The centrifuge was operated under such conditions that most of the biomass solids was removed together with the supernatant. This treatment resulted in a suspension of 70w/w % natamycin (anhydrous basis) on dry matter. The natamycin yield was about 97%. A propanol solution was then added to obtain a natamycin suspension containing 35v/v % propanol. A NaOH solution was added to increase the pH of the suspension to 10.4 in order to dissolve the natamycin. Subsequently, the natamycin solution was filtered using a membrane filter press equipped with filter cloth having a pore size of at least 10 µm. Subsequently, the filter cake was washed using a 35v/v % propanol solution. After the membrane filtration, a depth filtration was performed using a pore size of 0.25 microns. Subsequently, the depth filtration filters were washed using a 35v/v % propanol solution. After the depth filtration, the pH of the filtrate was lowered to 6.0 by reducing the pH 0.3 pH units per 5 minutes by adding hydrochloric acid in order to precipitate the natamycin from said filtrate. Subsequently, the mother liquor was then removed by membrane filtration. To further reduce the water content, the crystals were washed using a propanol solution. The produced natamycin cake was dried using a vacuum dryer. The dried crystals were then micronised to between 1 to 10 micrometers.

Example 3

Comparison of the Release Rate of the Natamycin of the Invention with Natamycin of the Prior Art Using the method described in example 1, the release rate profile of the new slow release natamycin was compared to the release rate profile of known commercial natamycin Delvocid® (DSM, The Netherlands). Suspensions of the natamycin preparations were prepared in such a manner that each suspension contained 800 ppm natamycin as such. 50 µl of each of the respective mixtures was applied on a paper filter disc and the release rate was analysed using the method of example 1. The results are summarized in the following tables.

TABLE 1

Initial release rate (40 µg carrier loading)

|  | Release rate after 24 hours (µg/24 hours) | Release rate after 48 hours (µg/24 hours) |
|---|---|---|
| Low release natamycin | <2 | <1.8 |
| Delvocid ® | <3 | <2 |

TABLE 2

Decrease in release rate after 9 days

|  | % decrease in release rate |
|---|---|
| Low release natamycin (10 µg carrier loading) | 35 |
| Low release natamycin (40 µg carrier loading) | 45 |
| Delvocid ® (40 µg carrier loading) | 58 |

TABLE 3

| | Release rate after 11 days |
|---|---|
| | Release rate ($\mu g$/24 hours) |
| Low release natamycin (5 $\mu g$ carrier loading) | 0.35 |
| Low release natamycin (10 $\mu g$ carrier loading) | 0.6 |
| Low release natamycin (40 $\mu g$ carrier loading) | 1.2 |
| Delvocid ® (10 $\mu g$ carrier loading) | 1.1 |

The slow release natamycin according to the invention clearly has a lower release rate than a commercially available natamycin preparation (Delvocid®).

Example 4

Comparison of the Release Rate of the Natamycin of the Invention with Natamycin of the Prior Art in Beverages The release rate of the new slow release natamycin was compared with that of known commercial natamycin Delvocid® Instant (DSM, The Netherlands) by measuring their chemical stability in various beverages. The natamycin preparations were suspended in beverages to a final concentration of 150 to 170 ppm natamycin. The natamycin containing beverages were stored at 4° C. and the natamycin concentration in the beverage was measured in time. The results are summarized in the following tables.

TABLE 1

| | Details of beverages | |
|---|---|---|
| Beverage | Manufacturer | pH |
| Tomato juice | Appelsientje (J44E3 34:38), Friesland Foods, The Netherlands | 4.2 |
| Ice tea | Plus Supermarket (05125SE25056), The Netherlands | 3.2 |

TABLE 2

| | | Natamycin degradation in beverages | | |
|---|---|---|---|---|
| | | Total degradation (ppm) | | |
| Beverage | Time (weeks) | Slow release natamycin | Natamycin from Delvocid ® Instant | Difference |
| Tomato juice | 1 | 5.1 | 8.6 | 3.5 |
| | 2 | 13.1 | 13.7 | 0.6 |
| | 3 | 20.1 | 26.5 | 6.4 |
| | 4 | 23.2 | 27.9 | 4.7 |
| | 5 | 28.9 | 32.6 | 3.7 |
| Ice tea | 1 | 3.4 | 14.9 | 11.5 |
| | 2 | 5.4 | 15.5 | 11.1 |
| | 3 | 3.2 | 15.3 | 12.1 |
| | 4 | 15.0 | 28.2 | 13.2 |
| | 5 | 17.4 | 31.7 | 14.3 |

The data show that less slow release natamycin than natamycin in Delvocid® Instant is degraded in tomato juice and ice tea. Since only the dissolved fraction of a natamycin formulation is susceptible to degredation, the results indicate that the dissolved fraction of slow release natamycin is smaller than that of natamycin in Delvocid® Instant. Hence, the release rate of slow release natamycin is lower than that of Delvocid® Instant in both beverages.

The invention claimed is:

1. Natamycin having a release rate of 0.1-2.0 $\mu g$/24 hours over the first 24 hours when contacted on a carrier with an agar surface of 0.6 cm diameter at 6° C. and a carrier loading of 40 $\mu g$ of natamycin,
   wherein the natamycin is produced from a fermentation broth containing biomass and natamycin,
   wherein said process comprises:
   (a) disintegrating the biomass;
   (b) separating the natamycin from the thus treated fermentation broth to obtain a natamycin suspension, wherein said fermentation broth comprises the biomass and natamycin;
   (c) adjusting the pH of the natamycin suspension to a value greater than 10 and adding an amount of a substantially water-miscible solvent sufficient to dissolve the natamycin in said natamycin suspension;
   (d) removing insoluble solids from said pH-adjusted natamycin solution;
   (e) lowering the pH of said solution obtained in step (d) to a pH of 5 to 8 to precipitate the natamycin;
   (f) removing the natamycin from said natamycin suspension;
   (g) optionally, drying of the said removed natamycin; and
   (h) optionally, reducing the size of the said dried natamycin.

2. An antifungal composition comprising natamycin according to claim 1.

3. An antifungal composition according to claim 2, wherein the composition further comprises a water-miscible solvent.

4. An antifungal composition according to claim 2, wherein the composition additionally comprises at least another antimicrobial agent selected from the group consisting of a weak acid preservative, sulphur dioxide, sulphite, nitrate, nitrite, dimethyl dicarbonate, biphenyl, diphenyl, orthophenylphenol, thiobendazole, an inorganic acid, an imidazole and a bacteriocin.

5. A product treated with the antifungal composition of claim 2.

6. Method for preserving a product susceptible to fungal spoilage by treating the product with the antifungal composition of claim 2.

7. Natamycin having a release rate of 0.1-1.0 $\mu g$/24 hours over the first 24 hours when contacted on a carrier with an agar surface of 0.6 cm diameter at 6° C. and a carrier loading of 10 $\mu g$ of natamycin,
   wherein the natamycin is produced from a fermentation broth containing biomass and natamycin,
   wherein said process comprises:
   (a) disintegrating the biomass;
   (b) separating the natamycin from the thus treated fermentation broth to obtain a natamycin suspension, wherein said fermentation broth comprises the biomass and natamycin;
   (c) adjusting the pH of the natamycin suspension to a value greater than 10 and adding an amount of a substantially water-miscible solvent sufficient to dissolve the natamycin in said natamycin suspension;
   (d) removing insoluble solids from said pH-adjusted natamycin solution;
   (e) lowering the pH of said solution obtained in step (d) to a pH of 5 to 8 to precipitate the natamycin;

(f) removing the natamycin from said natamycin suspension;
(g) optionally, drying of the said removed natamycin; and
(h) optionally, reducing the size of the said dried natamycin.

8. The natamycin of claim 7, wherein the natamycin is produced from a fermentation broth containing biomass and natamycin, wherein said process comprises: drying of the said removed natamycin and reducing the size of the said dried natamycin, 9. The natamycin of claim 7, wherein the natamycin has a release rate of 0.8 of 1.0 µg /24 hours over the first 24 hours when contacted on a carrier with an agar surface of 0.6 cm diameter at 6° C. and a carrier loading of 10 µg of natamycin.

\* \* \* \* \*